United States Patent [19]

Sugden et al.

[11] Patent Number: 5,716,845
[45] Date of Patent: Feb. 10, 1998

[54] IMMORTALIZED LYMPHOCYTES FOR PRODUCTION OF VIRAL-FREE PROTEINS

[75] Inventors: William Maxwell Sugden, Madison, Wis.; Wolfgang Friedrich Hammerschmidt, Munich, Germany

[73] Assignee: Wisconsin Alumni Research Foundation, Madison, Wis.

[21] Appl. No.: 504,494

[22] Filed: Jul. 20, 1995

[51] Int. Cl.$^6$ .............................. C12N 5/10; C12N 15/85; C12N 15/86
[52] U.S. Cl. ................................... 435/372.2; 435/320.1
[58] Field of Search ........................... 435/320.1, 240.2, 435/69.1, 372.2, 6; 514/44

[56] References Cited

PUBLICATIONS

Orkin et al., *Report and Recommendations of the Panel to Assess the NIH Investment in Research on Gene Therapy*, NIH, 1995.

Farrell, Paul J., *Epstein–Barr Virus Genome*, Advances in Viral Oncology, vol. 8, edited by G. Klein. Raven Press, Ltd., New York ©1989, pp. 103–132.

Fixman, Elizabeth D. et al., *trans–Acting Requirements for Replication of Epstein–Barr Virus ori–Lyt*, Journal of Virology, vol. 66, No. 8, Aug. 1992, pp. 5030–5039.

Gardella, Thomas et al., *Detection of Circular and Linear Herpesvirus DNA Molecules in Mammalian Cells by Gel Electrophoresis*, Journal of Virology, vol. 50, Apr. 1984, pp. 248–254.

Hammerschmidt, Wolfgang et al., *Genetic analysis of immortalizing functions of Eptstein–Barr virus in human B lymphocytes*, Reprinted from Nature, vol. 340, No. 6232, Aug. 1989, pp. 393–397.

Heston, L. et al., *New Epstein–Barr virus variants from cellular subclones of P3J–HR–1 Burkitt lymphoma*, Nature, vol. 295, Jan. 14, 1982, pp. 160–163.

Kempkes, Bettina et al., *Immortalization of Human B Lymphocytes by a Plasmid Containing 71 Kilobase Pairs of Epstein–Bar Virus DNA*, Journal of Virology, vol. 69, No. 1, Jan. 1995, pp. 231–238.

Kieff, Elliott et al., *Epstein–Barr Virus and Its Replication*, Virology, Second Edition, edited by B. N. Fields, D. M. Skipe et al., Raven Press, Ltd., New York ©1990, pp. 1889–1920.

O'Connor, Michael et al., *Construction of Large DNA Segments in Escherichia coli*, Science, vol. 244, Jun. 16, 1989, pp. 1307–1312.

*Primary Examiner*—James Ketter
*Attorney, Agent, or Firm*—Merchant, Gould, Smith, Edell, Welter & Schmidt, P.A.

[57] ABSTRACT

This invention is directed to construction of recombinant plasmids that contain the Epstein-Barr virus ("EBV") genetic information involved in the immortalization of human lymphocytes, but that lack one or more genes implicated in EBV lytic replication. The recombinant plasmids have the advantage of being able to immortalize human lymphocytes, while being incapable of generating infectious EBV particles. The invention also provides human lymphocytes that have been successfully infected and immortalized by the recombinant plasmids. These human lymphocyte clones can be used as cellular factories to produce desired proteins and as delivery vehicles for gene therapy. Additionally, the invention establishes a method by which desired proteins can be produced in immortalized cellular factories, without generating infectious EBV particles. These proteins can be the normal cellular products of immortalized human lymphocytes, or they can be proteins encoded by foreign genes, which have been cloned into the lymphocytes.

11 Claims, No Drawings

IMMORTALIZED LYMPHOCYTES FOR PRODUCTION OF VIRAL-FREE PROTEINS

STATEMENT OF GOVERNMENT SUPPORT

This invention was made with United States government support from the National Institutes of Health, grant numbers CA 01775, AI29988, CA 22443. The United States Government has certain rights in this invention.

BACKGROUND OF THE INVENTION

A. Field of the Invention

This invention concerns recombinant DNA technology. It provides recombinant plasmids derived from the Epstein-Barr virus ("EBV") that can immortalize human lymphocytes while disabling them from producing infectious virus particles. The immortalized lymphocyte clones can then be used as cellular factories to produce virus-free proteins or as delivery vehicles for human gene therapy.

B. The Prior Art

The last decade has witnessed progress in the development and application of recombinant DNA techniques in eukaryotes. For example, retrovirus vectors have been developed to carry foreign genes into certain eukaryotic hosts. Progress has also been made in the development of vector systems suited for use with human B lymphocytes. Apart from their pure research applications, these advances have potential therapeutic applications. But further advances are needed. In particular, it is desirable to develop vectors that can immortalize human lymphocytes. Such immortalized cell lines could be used as cellular factories for production of desired proteins and as delivery vehicles for human gene therapy.

EBV has the ability to transform human lymphocytes into cell lines that proliferate indefinitely in culture. Because EBV has both latent and lytic replication cycles, however, human lymphocytes immortalized by EBV can produce infectious EBV particles whenever the resident latent EBV enters lytic replication. This risk of generating infectious particles makes cells immortalized by EBV unsuitable for therapeutic applications. There is thus a need to develop recombinant plasmids that contain EBV genetic information involved in the immortalization of human lymphocytes, but that lack one or more genes required for EBV lytic replication. And there is a further need to use such plasmids to produce immortalized human lymphocytes, which can generate desired proteins that are uncontaminated by infectious EBV particles.

SUMMARY OF THE INVENTION

This invention is directed to a recombinant plasmid, human lymphocytes immortalized by the recombinant plasmid, and a method of producing virus-free proteins useful in various therapeutic applications. The recombinant plasmid incorporates viral DNA that can immortalize human lymphocytes without permitting lytic replication of the source virus.

The recombinant plasmid is formed by cloning selected Epstein-Barr virus ("EBV") DNA segments onto a prokaryotic plasmid backbone. The recombinant plasmid includes genes and cis-acting elements that are involved in the immortalization of human lymphocytes or in EBV latent replication. The recombinant plasmid also lacks one or more genes involved in EBV lytic replication. Consequently, the plasmid retains the ability to immortalize human lymphocytes, while lacking the capacity to enter EBV lytic replication, and thus to produce infectious EBV particles. The plasmid is thus a useful vector for transforming human lymphocytes and for introducing foreign genes encoding desired products.

A second aspect of the invention provides human lymphocytes that have been successfully infected and immortalized by the recombinant plasmid of the invention. As human lymphocyte clones infected by the plasmid lack some of the genetic information involved in EBV lytic replication, the clones are inherently incapable of generating and releasing infectious EBV particles. The human lymphocyte clones can therefore be used as cellular factories for the production of desired proteins and as delivery vehicles for human gene therapy.

A third aspect of the invention concerns a method of producing desired proteins that are uncontaminated by infectious EBV particles. The method has several variations. In one variation, immortalized human lymphocytes are simply used as cellular factories to produce protein products—either antibodies or lymphokines. To produce antibodies of a desired specificity, B lymphocytes must be obtained from an ill or antigenically challenged person. The resulting B-cell clones are then screened using well-established immunological techniques to identify clones that produce antibodies with desired specificities. These antibodies can then be used to foster passive immunity.

Another variation of the method involves cloning a gene—encoding a desired protein product—into the recombinant plasmid disclosed in this invention, or into the genome of human lymphocyte clones. Human lymphocytes immortalized by successful infection with the recombinant plasmid could produce the encoded protein without generating infectious EBV particles.

A third variation of the method disclosed in this invention involves using immortalized lymphocyte clones as vehicles for human gene therapy. This approach entails injecting immortalized cells into human recipients. The immortalized human lymphocytes would then produce desired proteins in situ, regardless of whether the proteins are antibodies, lymphokines, or the product of a foreign gene that was cloned into the plasmid. As the human lymphocytes would typically be drawn from the same person who would later receive the lymphocyte clones, complications resulting from the recipient's immunological recognition of the injected cells would be avoided.

DETAILED DESCRIPTION OF THE INVENTION

General Description

This invention encompasses a recombinant plasmid containing EBV genetic information involved in the immortalization of human lymphocytes, but lacking one or more genes implicated in EBV lytic replication. As the recombinant plasmid is incapable of lytic replication, it cannot produce infectious EBV particles. The invention also comprehends immortalized lymphocyte clones, which have been successfully infected by the recombinant plasmid of the invention. The invention additionally provides a method of producing a desired protein that is free of EBV infectious particles.

The Recombinant Plasmid

The invention provides a recombinant plasmid containing EBV genes and cis-acting elements involved in the immortalization of human lymphocytes and in latent replication of the plasmid. The recombinant lacks one or more EBV genes involved in EBV lytic replication. As the recombinant plasmid contains only a portion of the EBV genome, it is called a mini-EBV.

The lymphocyte immortalizing EBV genes that are included in the recombinant plasmid are LMP1, EBNA2, EBNA3a, EBNA3c, and EBNA1. For disclosure and further description of these genes, see Bettina Kempkes et al., *Immortalization of Human B Lymphocytes by a Plasmid Containing 71 Kilobase Pairs of Epstein-Barr Virus DNA,* 61 J. of Virol. 231–38 (Jan. 1995) (hereinafter "Kempkes et al."); see also Paul J. Farrell, Tumorigenic DNA Viruses, in 8 *Advances in Viral Oncology* 103–27 (George Klein ed. 1989); Elliot Kieff & David Liebowitz, Epstein-Barr Virus and Its Replication, in 2 *Fields Virology* 1889–1920 (Bernard N. Fields et al. eds., 2d ed. 1990). Each of these articles is hereby incorporated by reference. The LMP2a, LMP2b, EBER1, EBER2, EBNALP, and EBNA3b genes may be included in the recombinant plasmid as well, but human lymphocytes can be immortalized without them.

The cis-acting elements present in the recombinant plasmid are TR, oriP, and oriLyt. OriLyt permits the recombinant plasmid to be packaged, with the assistance of helper cells, into virus particles that can more readily infect human lymphocytes. Kempkes et al., cited above, identifies and describes these genetic elements, and that disclosure is herein incorporated by reference. The recombinant plasmid also lacks one or more of the genes that are implicated in EBV lytic replication. The genes are BALF5, BALF2, BMRF1, BSLF1, BBLF4, BBLF 2/3, BcLF1, BZLF1, BRLF1, and BMLF1. The absence of any one of these genes results in a recombinant plasmid that is inherently incapable of lytic replication. Elizabeth D. Fixman et al., *trans-Acting Requirements for Replication of Epstein-Barr Virus OriLyt,* 66 J. of Virol. 5030 (Aug. 1992), describes these genes in detail—including their functions and locations, and this disclosure is herein incorporated by reference. The various EBV genes discussed above, the presence or absence of which in part defines the invention, have been discussed in the prior art and are well-characterized. See generally id.; Paul J. Farrell, Tumorigenic DNA Viruses, in 8 *Advances in Viral Oncology* 103–27 (George Klein ed. 1989); Elliot Kieff & David Liebowitz, Epstein-Barr Virus and Its Replication, in 2 *Fields Virology* 1889–1920 (Bernard N. Fields et al. eds., 2d ed. 1990) (each of which is herein incorporated by reference).

A. Making the Recombinant Plasmid

All materials used in constructing the recombinant plasmid are commercially available unless otherwise noted. The recombinant plasmid is constructed by cloning EBV genes and cisacting elements involved in latent replication and human lymphocyte immortalization onto a prokaryotic plasmid backbone using well-known cloning techniques. The prokaryotic plasmid backbone comprises a prokaryotic plasmid that has been striped of all functionally significant genes, with the remaining DNA serving as a receptacle for other DNA sequences that are cloned onto the prokaryotic plasmid. A cloning technique called multi-step chromosomal building is especially preferred because it permits large but deliberately selected EBV segments to be added to the prokaryotic backbone. For a detailed discussion of this technique, see O'Connor et al., *Construction of Large DNA Segments in Escherichia coli.,* 244 Science 1307–1312, which is herein incorporated by reference. The technique involves sequential addition to an initial plasmid of partially-overlapping DNA segments, each of which is added via a different shuttle vector plasmid. See Id. and Kempkes et al., 61 J. of Virol. at 232–33, both of which are herein incorporated by reference. The chromosomal building technique thus allows the stepwise construction of a recombinant plasmid with a definite composition.

Using the preferred chromosomal building technique, the recombinant plasmid is constructed by cloning large but deliberately selected regions of the EBV genome into an F-factor, *E. coli*-based plasmid. Nine plasmids from the immortalized-competent B95-8 strain of EBV are established in *E. coli*. The F-factor plasmid p931.12 serves as the recipient for homologous recombination in *E. coli* with the next shuttle plasmid, namely p935.1.

In the preferred embodiment, the p935.1 plasmid and all other recombinant plasmids are generated using the pMBO96 cloning vector. Homologous recombinations are carried out in recA+ *E. coli* RVsmc or in recA *E. coli* CBTS carrying a recA amber allele and a temperature-sensitive amber suppressor. Intermediate plasmids are resolved through use of a resD expression plasmid via the two rfsF sites present in the cointegrate, and the F-factor prokaryotic backbone is retained along with the EBV recombined insert. Partially-overlapping plasmids are added in consecutive steps, with each plasmid adding a DNA segment that joins the growing recombinant backbone structure through homologous recombination.

The p1244.8a recombinant plasmid resulting from the preferred approach includes the LMP1, LMP2a, LMP2b, EBER1, EBER2, EBNA-LP, EBNA2, EBNA3a, EBNA3b, EBNA3c, and EBNA1 genes and the TR, oriP, and OriLyt cis-acting elements. But the p1244.8a plasmid lacks the BALF5, BALF2, BBLF 2/3, and BcLF1 genes. As each of these four genes is involved in EBV lytic replication, plasmid p1244.8a is incapable of lytic replication and is thus incapable of producing infectious EBV particles. The disablement of EBV lytic replication, however, could be accomplished by omitting any set of one or more genes that are involved in EBV lytic replication.

Recombinant plasmids capable of both initiating and maintaining immortalization of human lymphocytes without helper virus assistance can be created by rescuing the recombinant plasmid from lymphocyte clones that lack any detectable trace of helper virus. For more details see Kempkes et al., 61 J. of Virol. at 233, which is hereby incorporated by reference. The capacity of the rescued plasmids to initiate and maintain immortalization of human lymphocytes can be tested by exposing the lymphocytes to serial dilutions of virus stocks, plating the infected cells in a semisolid medium, and plotting the number of proliferating colonies as a function of serial dilutions of viral stocks. Resulting "one-hit kinetics" reveal whether a single recombinant plasmid can effect immortalization without helper virus assistance. For more details see Kempkes et al., 61 J. of Virol. at 233, which is hereby incorporated by reference.

B-lymphocyte clones lacking any traces of P3HR1 helper virus may be studied by rescuing their respective mini-EBVs into *E. coli* and sequencing them. Extensive analysis of these rescued plasmids reveals that their structures are the same as the original, p1244.8a recombinant plasmid except at the EBNA3a locus. The altered plasmids are capable of initiating B-cell immortalization, indicating that the wild type EBNA3 gene is required for such initiation. Because these recombinant plasmids possess the intrinsic capacity to initiate, as well as to maintain, human lymphocyte immortalization, they are preferred. The wildtype ENBA3 gene was also be inserted into the p1244.8a by standard cloning techniques, and this approach is especially preferred.

In summary, any recombinant plasmid that incorporates the EBV genes that are involved in the initiation and maintenance of human lymphocyte immortality, but that lacks one or more of genes involved in EBV lytic replication, is within the present invention, regardless of the presence of any other genetic information. The invention is exemplified by but not limited to the F-factor plasmid system and shuttle vectors used in the preferred embodiment. Virtually any prokaryotic plasmid can be used, so long as suitable shuttle plasmids are established.

B. Using the Recombinant Plasmid

The recombinant plasmid provided by this invention can be used to immortalize human lymphocytes as discussed below. The plasmid can also be used as a vector to carry foreign genes into human lymphocytes. The recombinant plasmid can also be used as a research tool to elucidate further the process of immortalization and the EBV latent and lytic replication cycles.

Immortalized Human Lymphocytes

A second aspect of the invention provides human lymphocyte clones that have been infected and immortalized by the recombinant plasmid discussed above and disclosed in this invention. As the clones lack some of the genetic information involved in EBV lytic replication, they are inherently incapable of generating and releasing infectious EBV particles. The human lymphocyte clones can therefore be used as cellular factories for the production of desired proteins and as delivery vehicles for human gene therapy.

A. Making Immortalized Human Lymphocytes

Human lymphocytes are generally resistant to the uptake and expression of DNA. For ease of use, the recombinant plasmid is packaged or "encapsulated" into a viral particle to infect human lymphocytes. The incorporation of the oriLyt and TR (terminal repeats) cis-acting elements into the recombinant plasmid allows amplification and subsequent packaging of the plasmid.

OriLyt is the EBV origin for lytic replication. See *Lytic Origin of Replication for Epstein-Bart Virus (EBV)*, U.S. Pat. No. 5,194,601, issued Mar. 16, 1993, the disclosure of which is herein incorporated by reference. The presence of oriLyt in the recombinant plasmid allows it to be amplified. The presence of TR (terminal repeats) elements allow the amplified plasmid to be cleaved and packaged into virus particles by lymphoblastoid helper cells containing endogenous helper virus. For details, see W. Hammerschmidt and B. Sugden, 340 Nature at 393, which is hereby incorporated by reference. Once encapsidated, the recombinant plasmid can more readily infect human lymphocytes.

A helper cell line is a clone of cells that is latently infected with a nonimmortalizing strain of EBV that has all transacting genes necessary to replicate and package the recombinant plasmid. See Kempkes et al., 61 J. of Virol. at 232–33, the disclosure of which is herein incorporated by reference. In a preferred embodiment, a het-free cell clone of P3HR1-infected Burkitt's lymphoma, called the HH514 helper cell clone is used. See L. Heston, *New Epstein-Barr Virus Variants from Cellular Subclones of P3J-HR-1 Burkitty Lymphoma*, 295 Nature 160–63 (1982), which is herein incorporated by reference. These HH514 helper cells are grown in RPMI medium supplemented with 10% fetal calf serum.

The recombinant plasmid is introduced into suitable helper cells by electroporation or other appropriate technique. For further clarification, see Kempkes et al., 61 J. of Virol. at 232–33, the disclosure of which is herein incorporated by reference. The plasmid is preferably introduced together with the virus trans-acting gene BZLF1 to induce the lytic phase of the EBV life cycle. After several days, the virus particles that have been released from the lysed cells are harvested. Id. Each virus particle contains either genomic helper virus DNA, encapsidated copies of the recombinant plasmid, or possible recombinations between the two. The virus stock is filtered to remove cells, and used to infect human lymphocytes: preferably primary human B lymphocytes. The B cells may be harvested from cord blood, buffy coat fractions of adult peripheral blood, or other well-known sources.

After being exposed to the virus particles, the human lymphocytes are plated at limiting dilution on a lethally irradiated human fibroblast feeder cell layer. Immortalized lymphocyte clones develop from lymphocytes that were infected by the recombinant plasmid, alone or in conjunction with the helper virus, but not from cells that were infected by the helper virus alone. To determine whether clones of immortalized lymphocytes contain the recombinant plasmid alone or in combination with helper virus DNA, standard Southern blot and PCR analyses are used to screen the clones. For details concerning these well-known analyses, see KemDkes, 61 J. of Virol. at 232–33, which is herein incorporated by reference. Clones can be found that do not contain any detectable traces of helper virus, with a level of sensitivity using the PCR analysis of fewer than 5 molecules of helper virus DNA per 30,000 cell genomes. The clones are stably immortalized.

Unencapsidated recombinant plasmid can also be introduced into B lymphocytes directly by electroporation, or some other suitable technique. Proliferating B-cell clones arise in culture following introduction of the naked plasmid DNA, but less efficiently than when the recombinant plasmid is packaged or encapsidated before being used to infect the B cells. Inclusion of a packaging step is thus preferred.

However injected, the recombinant plasmid replicates extrachromosomally within the infected lymphocytes as expected. This can be demonstrated by application of the Gardella gel technique. See generally T. Gardella et al., *Detection of Circular and Linear Herpesvirus DNA Molecules in Mammalian Cells by Gel Electrophoresis*, 50 J. of Virol. 248–54 (1984), the disclosure of which is herein incorporated by reference.

B. Using Immortalized Human Lymphocytes

The invention provides human lymphocyte clones that have been successfully infected and immortalized by the recombinant plasmid. Although the clones are stably immortalized by the presence of EBV genes on the recombinant plasmid, the cells intrinsically lack the capacity to enter the EBV lytic phase and thus to produce infectious EBV particles. The immortalized human lymphocytes are thus eminently suited to the production of useful EBV-free proteins and as delivery vehicles in human gene therapy.

Method of Producing Desired Proteins that are Free of EBV Contamination

A third aspect of the invention concerns a method of producing desired proteins that are free of EBV infectious particles. The method embraces several variations: (1) production of a desired protein that is native to a human lymphocyte—generally an antibody or lymphokine, (2) production of a desired protein that is encoded by a foreign gene which has been introduced into a human lymphocyte, and (3) production of a desired protein—whether native or alien—wherein the immortalized host lymphocyte is actually inserted into a human recipient so that the protein is produced and delivered in situ.

All three variations entail infecting human lymphocytes with a recombinant plasmid containing EBV genetic information involved in the immortalization of human lymphocytes, but lacking one or more genes implicated in EBV lytic replication. All three variations thus involve constructing a recombinant plasmid according to the techniques discussed above or other well-known cloning techniques. Alternatively, the recombinant plasmid can be obtained commercially.

However obtained, the recombinant plasmid is then introduced into helper cells by electroporation or some other appropriate technique as discussed above, and the lytic phase of EBV replication is induced. After several days, the encapsidated EBV virus particles are harvested and can be used to infect human lymphocytes. The three method variations are also different in important respects.

The first variation involves using immortalized lymphocytes to produce large amounts of their common protein products, namely antibodies or lymphokines. In the case of antibodies, the method preferably demands that the human B cells be drawn from antigenically challenged individuals, so that antibodies of the desired specificity can be produced. For example, to generate antibodies specific for antigens of the HIV virus, the B cells would be drawn from HIV-positive persons. These B cells would then be immortalized through infection with the recombinant plasmid of the invention, as discussed above.

The resulting immortalized B-cell clones would then be screened, using well-known immunological techniques, to identify clones that produce antibodies specific to the relevant HIV epitopes. See E. Harlow and D. Lane, *Antibodies* at pp. 139–241 (Cold Spring Harbor Laboratory, 1988), which is hereby incorporated by reference. The desired B-cell clones would have to be subjected to limiting dilutions and repeated Southern blot and PCR analyses to ensure complete absence of HIV DNA. See id. To conduct these analyses, DNA fragments derived from the HIV virus would have to be available. This method variation is generalizable: it provides a means of producing monoclonal antibodies specific for the epitopes of virtually any well-known pathogen. The antibodies can then be used to establish passive immunity in human patients or for experimental purposes.

The second method variation involves cloning a foreign gene encoding a desired protein product into the recombinant plasmid described above or into the genome of the host lymphocyte. Any well-known cloning technique can be used to insert the desired gene. See J. Sambrook et al., *Molecular Cloning* (Cold Spring Harbor Laboratory, 1989), which is hereby incorporated by reference. This method variation permits mass production by immortalized human lymphocytes of the protein encoded by the cloned gene. See Example 5 infra, for more detail.

A third variant of the method involves injecting immortalized human lymphocytes into human recipients. The immortalized human lymphocytes can then produce the desired protein in situ, whether that product consists of antibodies, lymphokines, or the product of a cloned gene. As the primary human lymphocytes employed in the method will generally be obtained from the same person who later receives the immortalized lymphocyte clones, immunological recognition by the recipient's immune system is avoided. For details, see K. W. Culver, *Gene Therapy*, chapter 4 (Mary Ann Liebart, 1994), which is incorporated by reference; see also Example 6, infra.

In this invention, recombinant plasmids containing all EBV genetic elements involved in the immortalization of human lymphocytes, but lacking one or more genes essential to EBV lytic replication, were generated. These recombinant plasmids have the ability to initiate and maintain immortalization in human lymphocytes, however, they intrinsically lack the capacity to enter the lytic replication cycle and thus to produce infectious EBV particles. The invention also provides immortalized human B lymphocytes that have been successfully infected with such recombinant plasmids. Additionally, the invention provides a method of producing a desired protein that is free of EBV infectious particles.

The present invention is not limited to the particular species of recombinant plasmids described in the preferred embodiments. Rather, the invention comprehends any recombinant plasmid containing the EBV genes necessary for initiation and maintenance of immortalization, but lacking one or more genes needed for lytic replication, regardless of the presence of additional genetic information, or the spatial order of the genes contained in the recombinant plasmid. These observations and reservations—made in reference to the claimed recombinant plasmid—apply perforce to the immortalized human lymphocytes and methods also advanced in the attached claims.

EXAMPLE 1

Construction of the p1244.8a Plasmid

Plasmid p1244.8a was constructed by cloning large but deliberately selected portions of the EBV genome into an F-factor plasmid using the chromosomal building technique. Nine plasmids from the immortalized-competent B95-8 strain of EBV were established in *E. coli*. The F-factor plasmid p931.12 served as the recipient for homologous recombination in *E. coli* with the next shuttle plasmid, namely p935.1. The p935.1 plasmid and all other recombinant plasmids were generated using the pMBO96 cloning vector.

Homologous recombinations were carried out in recA+ *E. coli* RVsmc or in recA *E. coli* CBTS carrying a recA amber allele and a temperature-sensitive amber suppressor. Combined plasmids were resolved through use of a resD expression plasmid via the two rfsF sites present in the cointegrate, the F-factor prokaryotic backbone being retained together with the EBV recombined insert. Neighboring, partially-overlapping plasmids were added in consecutive steps. The added plasmids sequentially joined the growing recombinant backbone structure through homologous recombination and the resulting plasmids were then resolved.

The p1244.8a plasmid that ultimately resulted from the multi-step chromosomal building technique is 83,851 bp long, including the prokaryotic backbone and a marker gene that plays no role in the invention. The total EBV DNA added amounted to 71 kbp of the EBV genome, which is itself approximately 165 kbp long. Plasmid p1244.8a includes the LMP1, LMP2a, LMP2b, EBER1, EBER2, EBNA-LP, EBNA2, EBNA3a, EBNA3b, EBNA3c, and EBNA1 genes and the TR, oriP, and OriLyt cis-acting elements. The p1244.8a plasmid lacks the BALF5, BALF2, BBLF 2/3, and BcLF1 genes. Plasmid p1244.8a is thus inherently incapable of supporting EBV lytic replication. It is, however, capable of maintaining B-cell immortality.

EXAMPLE 2

Immortalization of Human B Lymphocytes

The p1244.8a plasmid was constructed as detailed in example 1 and elsewhere in the specification. Samples were purchased of the HH514 helper cell clone, which is a het-free cell clone of the P3HR1 Burkitt's lymphoma cell line. Ten micrograms of plasmid p1244.8a DNA was transiently introduced into HH514 cells by electroporation together with 10 μg of pCMV-BZLF1 to induce the lytic life cycle. The HH514 helper cells were grown in RPMI medium supplemented with 10% fetal calf serum. Released virus particles were harvested 5 days later.

The virus particles released from the lysed helper cells contained either genomic P3HR1 helper virus DNA, encapsidated copies of p1244.8a, or possible recombinations between them. This virus stock was then sterilized, filtered, and used to infect primary human B cells derived from cord blood or buffy coat fractions of adult peripheral blood.

The infected B cells were then plated at limiting dilution in 96-well cluster plates on a lethally irradiated human fibroblast feeder cell layer. Immortalized B-cell clones developed from B cells that were infected by the p1244.8a plasmid, but not from cells that were infected by P3HR1 helper virus alone. These B cell clones have proven to be stably immortalized.

EXAMPLE 3

Rescuing the p1244.8a-6.6 and p1244.8a-8.4 Plasmids

In initial experiments, seven of forty-seven immortalized B cell clones were found to lack any detectable trace of P3HR1 helper virus. Additionally, one clone that was doubly infected by both p1244.8a and P3HR1 DNA gradually lost the helper virus DNA over time. These observations raised the possibility that p1244.8a was capable of initiating immortalization in the absence of P3HR1.

Adult B lymphocytes were exposed to serial dilutions of virus stocks including virus particles containing p1244.8a. The infected cells were plated in a semisolid medium, and the number of proliferating colonies were plotted as a function of viral stock serial dilutions. The results revealed "two-hit kinetics", indicating that a single p1244.8a plasmid is unable to initiate immortalization. The P3HR1 helper virus must accompany p1244.8a to initiate proliferation of B lymphocytes.

Two of the B-cell clones that lacked detectable traces of P3HR1 helper virus were studied further by rescuing their respective mini-EBVs into E. coli and sequencing them. Extensive analysis of these plasmids indicate that their structures are the same as the p1244.8a parental plasmid except at the EBNA3 locus. The two altered plasmids were rescued from the Be253.30 and Be253.33 cell clones and were designated p1244.8a-6.6 and p1244.8a-8.4 respectively. These altered plasmids proved capable of both initiating and maintaining B cell immortalization, indicating that the wild type EBNA3 gene is very much involved in such initiation. Plasmids capable of initiating and maintaining B-cell immortality were also made by cloning a wild type EBNA3 gene into p1244.8a.

EXAMPLE 4

Generating Antibodies Specific for the HIV Envelope Protein Using Immortalized B Cells To generate immortalized B cells that secrete antibodies specific for the HIV envelope protein, B cells from an HIV-positive donor would be infected with the packaged recombinant plasmid of the invention. The infected cells would then be plated in microliter dishes, on an irradiated feeder layer, under conditions of limiting dilutions. Each well with proliferating B-cell clones would then be tested for antibodies specific to the HIV-envelope protein, using ELIZA or some other suitable immunological assay.

Wells with clones testing positive would be subcloned into microliter dishes and tested again for the presence of antibodies with appropriate specificities. This process would be repeated until all cloned progeny from an identified well are found to secrete antibodies to HIV envelope protein. The useful clones are then screened by PCR to detect the presence of unwanted EBV lytic genes and HIV. Only cells that are free of these contaminants are used further. The techniques cited in this example are well-established. See E. Harlow and D. Lane, Antibodies at pp. 139–241 (Cold Spring Harbor Laboratory, 1988), which is incorporated by reference.

EXAMPLE 5

Cloning a Foreign Gene into Human B Lymphocytes Using p1244.8a

The tissue plasminogen activator (TPA) gene with its translatimal terminator could be cloned into one of the plasmid derivatives used to construct the recombinant plasmid. The TPA gene would have to be cloned behind an efficient promoter: the immediate early promoter of human cytomegavirus would work.

One possible site within the recombinant plasmid that can accommodate foreign expressed genes lies between the open reading frames for EBNA-1 and LMP. Approximately 50 kbp of EBV DNA has been removed from this region in the recombinant plasmid, and no required transcription traverses this region in wild-type EBV. A plasmid derivative (for example, of p1242.1) could be constructed that contains and expresses TPA. This derivative could then be used in the multistep chromosomal building technique, so that the TPA gene would be incorporated into the region between EBNA-1 and LMP of the p1244.8a plasmid. For a detailed description of the techniques used to construct and test a recombinant plasmid derivative containing a foreign gene, see J. Sambrook et al., Molecular Cloning (Cold Spring Harbor Laboratory, 1989), which is incorporated by reference.

EXAMPLE 6

Using Immortalized Human B Lymphocytes as Vectors for Human Gene Therapy

B lymphocytes from a patient with a deficiency in adenine deaminase (ADA) would be infected with a recombinant plasmid into which the human gene for ADA is cloned and efficiently expressed, according to the techniques described in Example 5. Immortalized cells would be analyzed for levels of ADA expression by testing for both the protein and RNA, as described in J. Sambrook et al., Molecular Cloning (Cold Spring Harbor Laboratory, 1989), which is incorporated by reference. B-cell clones that both lacked helper virus and expressed desired levels of ADA could then be reintroduced into the patient to provide therapeutic levels of ADA in situ. For details, see K. W. Culver, Gene Therapy, chapter 4 (Mary Ann Liebart, 1994), which is incorporated by reference.

These and other objects and advantages of the present invention are discussed, illustrated, and supported by the foregoing summary and detailed description, including the examples and preferred embodiments. The embodiments do not, however, define the full scope of the invention. Rather, the invention is defined primarily by reference to the accompanying claims.

We claim:

1. A recombinant plasmid comprising:
    a prokaryotic plasmid backbone joined to a DNA segment comprising a set of EBV genes including LMP1, EBNA2, EBNA3a, EBNA3c, and EBNA1, and a set of EBV cis-acting elements including TR, oriP, and oriLyt;
    wherein the recombinant plasmid is free of at least one EBV lytic gene selected from the group consisting of BALF5, BALF2, BMRF1, BSLF1, BBLF4, BBLF 2/3, BcLF1, BZLF1, BRLF1, and BMLF1, or combinations thereof.

2. A recombinant plasmid according to claim 1 wherein each included EBV gene is associated with its wild type EBV promoter.

3. A recombinant plasmid according to claim 2 wherein the EBV genes and cis-acting elements occur in the same order as they do in wild type EBV.

4. A recombinant plasmid according to claim 3 in which the prokaryotic backbone is derived from a F-factor based plasmid.

5. The recombinant plasmid according to claim 1 having the designation p1244.8a.

6. The recombinant plasmid according to claim 1 having the designation p1244.8a-6.6.

7. The recombinant plasmid according to claim 1 having the designation p1244.8a-8.4.

8. The recombinant plasmid according to claim 1 further comprising EBV genes selected from the group including LMP2a, LMP2b, EBER1, EBER2, EBNA-LP, and EBNA3b, or combinations thereof.

9. An Immortalized human lymphocyte comprising:
    a human lymphocyte that has been infected with a recombinant plasmid comprising:
        a prokaryotic plasmid backbone joined to a DNA segment comprising a set of EBV genes comprising LMP1, EBNA2, EBNA3a, EBNA3c, and EBNA1, and a set of EBV cis-acting elements comprising TR, oriP, and oriLyt;
        wherein the recombinant plasmid is free of at least one EBV lytic gene selected from the group consisting of BALF5, BALF2, BMRF1, BSLF1, BBLF4, BBLF 2/3, BcLF1, BZLF1, BRLF1, BMLF1, and combinations thereof.

10. An immortalized human lymphocyte according to claim 9 wherein the human lymphocyte used is a human B lymphocyte.

11. The immortalized human lymphocyte of claim 9 wherein the recombinant plasmid further comprises EBV genes selected from the group consisting of LMP2a, LMP2b, EBER1, EBER2, EBNA-LP, LP, EBNA3b, and combinations thereof.

* * * * *